US010946118B2

(12) United States Patent
O'Keeffe et al.

(10) Patent No.: US 10,946,118 B2
(45) Date of Patent: Mar. 16, 2021

(54) WOUND HEALING DEVICE

(71) Applicant: TheraDep Technologies, Inc., Palo Alto, CA (US)

(72) Inventors: Joe O'Keeffe, Fermoy (IE); Peter Dobbyn, Middleton (IE); John Gerard O'Donoghue, Dungarvan (IE); Liam O'Neill, Middleton (IE)

(73) Assignee: TheraDep Technologies, Inc., Palo Alto, CA (US)

( * ) Notice: Subject to any disclaimer, the term of this patent is extended or adjusted under 35 U.S.C. 154(b) by 0 days.

(21) Appl. No.: 15/882,335

(22) Filed: Jan. 29, 2018

(65) Prior Publication Data
US 2018/0154039 A1 Jun. 7, 2018

Related U.S. Application Data

(60) Continuation of application No. 14/795,221, filed on Jul. 9, 2015, now abandoned, which is a division of
(Continued)

(51) Int. Cl.
*A61L 26/00* (2006.01)
*H05H 1/42* (2006.01)
(Continued)

(52) U.S. Cl.
CPC ............. *A61L 26/0057* (2013.01); *A61L 2/14* (2013.01); *A61L 26/009* (2013.01);
(Continued)

(58) Field of Classification Search
None
See application file for complete search history.

(56) References Cited

U.S. PATENT DOCUMENTS

| 4,929,319 A | 5/1990 | Dinter et al. |
| 6,565,558 B1 * | 5/2003 | Lindenmeier ........ A61B 18/042 604/22 |

(Continued)

FOREIGN PATENT DOCUMENTS

| EP | 1705965 A1 | 9/2006 |
| EP | 2666544 A1 | 11/2013 |

(Continued)

OTHER PUBLICATIONS

Bogaerts et al., "Gas Discharge Plasmas and Their Applications," Spectrochimica Acta Part B, vol. 57, pp. 609-658 (2002).
(Continued)

*Primary Examiner* — Dominic Lazaro
(74) *Attorney, Agent, or Firm* — Bookoff McAndrews, PLLC

(57) ABSTRACT

A plasma coating device for treating a wound comprises a plasma chamber having: one or more electrodes, a gas supply inlet, a plasma outlet exposed to ambient pressure, and an ignition system operatively connected to the electrodes for providing a non-thermal equilibrium plasma within the plasma chamber. An aerosol delivery system is operable to introduce a bioresorbable material as an aerosol into the plasma, to produce a coating on the wound surface.

**14 Claims, 1 Drawing She

Related U.S. Application Data application No. 13/377,389, filed as application No. PCT/IB2010/001439 on Jun. 15, 2010, now abandoned.

(60) Provisional application No. 61/187,340, filed on Jun. 16, 2009.

(51) Int. Cl.

| | |
|---|---|
| *A61L 2/14* | (2006.01) |
| *H05H 1/48* | (2006.01) |
| *H05H 1/24* | (2006.01) |
| *A61L 2/00* | (2006.01) |
| *B05D 1/00* | (2006.01) |
| *A61B 18/04* | (2006.01) |

(52) U.S. Cl.
CPC ....... *A61L 26/0019* (2013.01); *A61L 26/0023* (2013.01); *A61L 26/0033* (2013.01); *A61L 26/0042* (2013.01); *A61L 26/0066* (2013.01); *H05H 1/2406* (2013.01); *H05H 1/42* (2013.01); *H05H 1/48* (2013.01); *A61B 18/042* (2013.01); *A61L 2/0011* (2013.01); *A61L 2300/254* (2013.01); *A61L 2300/258* (2013.01); *A61L 2300/404* (2013.01); *A61L 2300/412* (2013.01); *A61L 2300/606* (2013.01); *A61L 2300/64* (2013.01); *B05D 1/62* (2013.01); *H05H 2001/483* (2013.01); *H05H 2240/20* (2013.01); *H05H 2245/122* (2013.01)

(56) References Cited

U.S. PATENT DOCUMENTS

| | | | |
|---|---|---|---|
| 7,201,935 B1 | 4/2007 | Claude et al. | |
| 7,455,892 B2 | 11/2008 | Goodwin et al. | |
| 2002/0020024 A1 | 2/2002 | Schmitz et al. | |
| 2004/0176749 A1 | 9/2004 | Lohmann et al. | |
| 2006/0084158 A1* | 4/2006 | Viol .................... | A61B 18/042 435/173.1 |
| 2007/0029500 A1 | 2/2007 | Coulombe et al. | |
| 2008/0118734 A1 | 5/2008 | Goodwin et al. | |
| 2008/0199513 A1 | 8/2008 | Beretta et al. | |
| 2008/0237484 A1 | 10/2008 | Morfill et al. | |
| 2011/0159273 A1 | 6/2011 | Lukowski et al. | |
| 2012/0009231 A1 | 1/2012 | Herbert et al. | |
| 2015/0314036 A1 | 11/2015 | O'Keeffe et al. | |

FOREIGN PATENT DOCUMENTS

| | | | | |
|---|---|---|---|---|
| WO | 0228548 | A2 | 4/2002 | |
| WO | 03097245 | A2 | 11/2003 | |
| WO | 2005106477 | A2 | 11/2005 | |
| WO | 2005110626 | A2 | 11/2005 | |
| WO | WO-2005110626 | A2 * | 11/2005 | ............... B05D 1/62 |
| WO | 2006048650 | A1 | 5/2006 | |
| WO | 2006116252 | A2 | 11/2006 | |
| WO | WO 2007/106212 | A1 | 9/2007 | |
| WO | 2009101143 | A1 | 8/2009 | |
| WO | 2009146432 | A1 | 12/2009 | |
| WO | 2010022871 | A1 | 3/2010 | |
| WO | WO 2010/105829 | A1 | 9/2010 | |
| WO | WO 2012/080835 | A2 | 6/2012 | |
| WO | WO 2017/136334 | A1 | 8/2017 | |

OTHER PUBLICATIONS

Chekmareva et al., Bulletin of Experimental Biology and Medicine, 129: 392-395 (2000).

Fridman et al., "Comparison of Direct and Indirect Effects of Non-Thermal Atmospheric-Pressure Plasma on Bacteria," Plasma Processes and Polymers, vol. 26: pp. 370-375 (2007).

Fridman et al., Plasma Chem Plasma Process, 26: 425-442 (2006).

Guerin et al., "Plasma Polymerization of Thin Films: Correlations Between Plasma Chemistry and Thin Film Character", Langmuir, vol. 18 pp. 4118-4123 (2002).

International Search Report dated Nov. 16, 2010, in PCT/2010IB/001439.

Ladwig et al., "Atmospheric plasma deposition of glass coatings on aluminum", Surface & Coatings Technology, vol. 201, pp. 6460-6464 (2006).

Massarweh et al., "Electrosurgery: History, Principles, and Current and Future Uses", J. Am. Coll. Surg., vol. 202, pp. 520-530 (2006).

Mennel et al., "Helium (Argon) Plasma Coagulation in Neurosurgery. Morphology of Tissue Damage and Reparation," Exp Toxic Pathol, vol. 54, pp. 255-263 (2002).

Okazaki et al., "Appearance of stable glow discharge in air, argon, oxygen and nitrogen at atmospheric pressure using a 50 Hz source", J. Phys. D; Appl. Phys. vol. 26, pp. 889-892 (1993).

Reich et al., "Argon Plasma Coagulation (APC) for Endo-Urological Procedures: Ex-Vivo Evaluations of Hemostatic Properties", European Urology, vol. 44, pp. 272-276 (2003).

Roth et al., "Atmospheric Pressure Plasma Sources", Ch. 15, pp. 37-73 in Industrial Plasma Engineering, vol. 2: Applications to Non-thermal Plasma Processing, Institute of Physics Publishing (2001).

Supplementary European Search Report for European Application No. 10789079, dated Aug. 22, 2014 (2 pages).

Shoulders et al., "Collagen Structure and Stability," Annu. Rev. Biochem, vol. 78, pp. 929-959 (2009).

Department of Defense, Blast Injury Research Program Coordinating Office, "Minimizing the Impact of Wound Infections Following Blast-Related Injuries," 2016.

Heinlin et al. "Plasma Medicine: Possible Applications in Dermatology," *Journal of the German Society of Dermatology*, 8, pp. 1-9 (2010).

Laroussi, Mounir, "Plasma Medicine: A Brief Introduction," Plasma, 1, pp. 47-60 (2018).

Lloyd et al. "Gas Plasma: Medical Uses and Developments in Wound Care," Plasma Processes and Polymers, 7, pp. 194-211 (2010).

International Search Report in PCT/US2017/015805 dated Jun. 26, 2017 (5 pages).

U.S. Appl. No. 16/074,365 filed Jul. 31, 2018 (40 pages).

\* cited by examiner

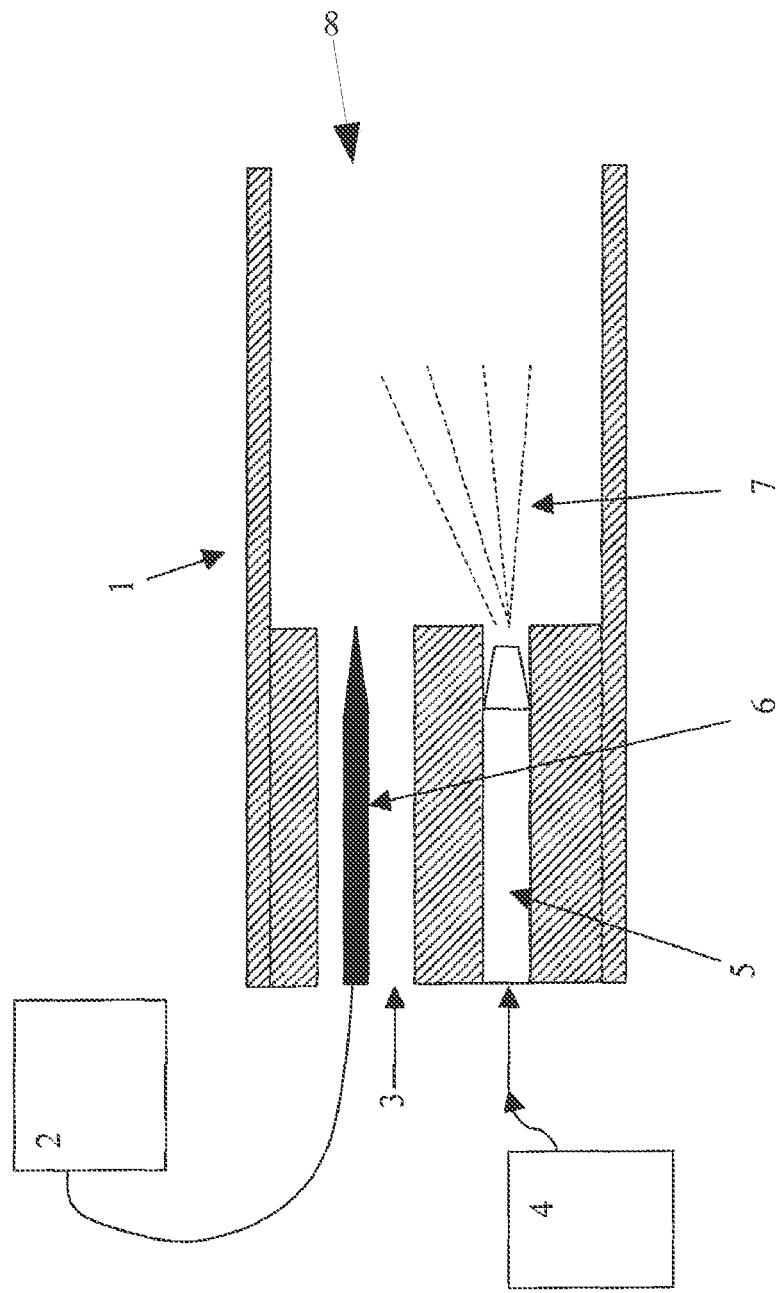

WOUND HEALING DEVICE

CROSS-REFERENCE TO RELATED APPLICATIONS

This application is a continuation of U.S. patent application Ser. No. 14/795,221, filed Jul. 9, 2015, which is a divisional of U.S. patent application Ser. No. 13/377,389, filed Dec. 9, 2011, which claims priority from PCT Application No. PCT/IB2010/001439, filed Jun. 15, 2010, which claims priority from U.S. Provisional Patent Application No. 61/187,340, filed Jun. 16, 2009, the entire contents of which are all incorporated herein.

BACKGROUND

Electrical plasma devices are well established in medicine. For example, Massarweb et al, J. Am. Coll. Surg., 2006, 202 (3), 520, discloses plasma devices for surgery; Reich et al, European Urology, 2003, 44 (2), 272-276, describe the use of an argon plasma (APC) to coagulate blood and stop bleeding; and Mennel et al, Experimental and Toxicological Pathology, 2002, 54 (3), 255, disclose using a helium plasma to obtain a similar response to the APC technique.

Plasmas can also be used to sterilise skin as disclosed in G. Fridman, A. D. Brooks, M. Balasubramanian, A. Fridman. A. Gustol, V. N. Vasilets, H. Ayan, G. Friedman, Plasma Process. Polym. 4 (2007) 370) and WO2006/116252. The use of plasma devices to promote wound healing has also been disclosed in US2008/0237484 and in WO2009/101143.

Outside of medicine, plasma devices are widely used to produce thin film coatings in industrial applications. Plasma polymers offer a number of advantages over conventional polymer coatings. The combination of reactive plasma and chemically active monomers produces a coating that is uniform, pin hole free and well bonded to the substrate. Furthermore, the curing can occur in a manner that is almost instantaneous, offering numerous processing advantages.

U.S. Pat. No. 4,929,319 describes a method for depositing a polymer coating in which an aerosol is introduced into a corona plasma and the reactive species thereby generated are allowed to deposit in a substrate that is also brought into the corona plasma.

WO 02/28548 describes a process in which an aerosol is introduced into an atmospheric pressure glow discharge (APGD) plasma and a coating is thereby formed on a substrate. The coating chemistry was found to be virtually unchanged from that of the precursor molecules by the exposure to the homogeneous APGD plasma.

WO2005/106477 describes a process for coating a substrate with a biomolecule in which the substrate is placed between two electrodes and a plasma is generated by applying an alternating current in which a positive voltage is applied to the first electrode and a zero voltage to the second electrode, and then a zero voltage to the first electrode and a negative voltage to the second electrode. A coating is then applied by introducing a reactive precursor to form a coating and biomolecules are simultaneously immobilised. The biomolecules may be introduced as an aerosol.

WO 05/110626 discloses coating a substrate with a polymer layer containing active agents. The method involves exposing a mixture of polymer forming materials (which react to form chemical bonds in a plasma) and active agents (which do significantly react in the plasma) to plasma. The polymer forming materials listed include various acrylates, alkenes and dienes that can be polymerised by the reactive species present within a plasma.

These prior documents rely on the plasma to induce the polymerisation of a monomer to produce the thin film or coating. The polymerisation can be driven through free radical (A. Bogaerts et al., Spectrochimica Acta Part B, 57 (2002) 609-658) or cationic reaction mechanisms (Daniel C. Guerin, David D. Hinshelwood, Sorin Monolache, Fcrencz S. Denes, and Vasgen A. Shamamian, Langmuir, 2002, 18 (10), pp 4118-4123).

Thus, while the methods described in WO 05/106477 and WO 05/110626 do allow for the deposition of polymers containing active agents, they are reliant upon the presence of a precursor which can react in the plasma to form the polymer coating during the deposition process. The requirement to induce reactions within the polymer precursor without damaging the active agent limits the degree of polymerisation that can be achieved.

SUMMARY OF THE INVENTION

The present invention provides a plasma device as claimed in claim 1.

In a further aspect, there is provided a non-thermal plasma treated bioresorbable material for use in coating a wound as claimed in claim 14.

In a still further aspect there is provided a method of treating a wound according to claim 22.

In embodiments of the present invention, a non-thermal plasma is applied to a wound. The plasma can sterilise the area, coagulate blood and deposit a bioresorbable coating to seal the wound area. The coating can further include active compounds to aid in wound healing.

The bioresorbable material can include blood plasma, chitosan or collagen, but may alternatively or in addition include a protein, a biopolymer (such as chitin, alginates, cellulose or hyaluronan), or a synthetic biodegradable polymer (such as poly (lactic-co-glycolic acid) (PLGA), polylactic acid, polycaprolactone, polyglactin) or a mixture of such materials.

Preferably, the bioresorbable material is introduced into a non-thermal plasma as a pre-cursor in the form of an aerosol. The bioresorbable material pre-cursor can either be dissolved or dispersed in a suitable carrier liquid.

Preferably, the active compound, for example, drug, enzyme, cell, protein or DNA may be either introduced into the plasma dissolved in the bioresorbable material pre-cursor or introduced separately.

In such implementations, the active compound is incorporated alongside a pre-polymerised polymer which allows the polymerisation and film forming steps to be separated out and provides a greater degree of process control.

The mixture of bioresorbable material, active compound and plasma further interact to produce a coating on the wound surface. The wound can either directly contact the plasma or can be placed downstream of the plasma chamber outlet.

In one embodiment, blood constituents are nebulised into the plasma, to deposit a layer of coagulated blood or blood plasma onto a wound surface.

BRIEF DESCRIPTION OF THE DRAWINGS

Embodiments of the invention will now be described, by way of example, with reference to the accompanying drawing, in which:

FIG. 1 is a schematic view of a plasma device in accordance with an embodiment of the present invention.

DESCRIPTION OF THE PREFERRED EMBODIMENTS

Referring now to FIG. 1, there is shown a schematic view of a plasma device according to an embodiment of the invention. The device includes a plasma chamber 1 including a metal electrode 6 to which a high voltage power supply/ignition system 2 is operatively connected. The chamber 1 further includes a gas inlet port 3 through which a supply of gas, for example, helium, argon or nitrogen or mixtures thereof is fed in operation of the device and which in combination with the ignition system causes a plasma to be struck and to stream from an outlet 8 of the plasma chamber. In the illustrated embodiment, a liquid delivery system 4 is operatively connected to an inlet of the plasma chamber and an internal nebuliser 5 causes the supplied liquid to be sprayed 7 into the chamber 1 as an aerosol. In alternative embodiments, not shown, an external nebuliser feeds the aerosol to a region outside the plasma chamber where it interacts with the reactive species emanating from the outlet 8 of the plasma chamber before coating a wound over which the plasma device is being passed.

In embodiments of the present invention, the plasma device initially sterilises and coagulates the wound. Then, by providing an aerosol from the supply 4 containing a bioresorbable material which may also contain an active agent, and introducing that aerosol into a plasma chamber 1, or into the reactive species that exist downstream of the plasma chamber 1, the device produces a coating on the wound. If required, the sterilisation, coagulation and coating deposition can occur simultaneously. Deposition of such a coating enables the continuous interaction of the pro-healing materials with the wound and provides for enhanced wound healing. Furthermore, the coating seals the wound and limits the opportunity for further bacteria to infect the wound site.

The term wound can be taken to encompass all forms of damage to the skin or body including burns, cuts, tears, piercings, contusions, abrasions, lacerations, punctures, gun shots or other forms of injury to the body. It may also encompass infections or chronic wounds such as ulcers.

The invention described herein allows the introduction of bioresorbable material including: proteins such as collagen, fibrin or fibronecin; biopolymers such as hyaluronan, chitosan, alginates and cellulose; and also biodegradable synthetic polymers such as PLGA which do not form using the same vinyl polymerisation reactions favoured by conventional plasma reactions onto a wound site. The plasma may cross-link these materials to produce a dry coating, but the degree of cross-linking is limited and is not sufficient to alter the functionality of the deposited material.

Embodiments of the present invention employ non-thermal plasma devices where the plasma operates close to room temperature thus allowing the processing of temperature sensitive materials, without imposing a damaging thermal burden onto the material. Nonetheless, the hot electrons of the plasma create, through high-energy collisions, a rich source of radicals and excited species with a high chemical potential energy capable of chemical and physical reactivity. Non-thermal equilibrium plasmas can be created at ambient pressure and have been reviewed extensively by Roth (Roth J. R., Industrial Plasma Engineering, Volume 2 Applications to Non-thermal Plasma Processing, Institute of Physics Publishing, 2001, pages 37-73). Such plasmas include dielectric barrier discharges. Another non-thermal equilibrium plasma is the Atmospheric pressure glow discharge (APGD) as described by Okazaki et al (J. Phys. D: Appl. Phys., 26, 889-892 (1993)). These APGD plasmas have been described extensively by Roth as One Atmosphere Uniform Glow Discharge Plasmas (OUAGDP) and are found to operate from 0.5 to 40 kHz. Corona plasma devices can also operate in non-thermal equilibrium mode. Various plasma jets are also capable of operating in a "cold" or non-thermal equilibrium mode.

Embodiments of the present invention employ plasma devices operating at frequencies above 100 kHz, which is beyond the sensory threshold of a patient's nervous system. For optimum control, the plasma is operated below 500 kHz and may be pulsed on and off in a controlled fashion to minimise the energy delivered to the aerosol and patient. This enables controlled plasma reactions that preserve precursor functionality and do not damage or fragment sensitive active species.

Alternatively, the plasma can be contained between two electrodes, with a grounded electrode separating the person or object to be treated from the plasma, such that no significant voltage is applied to any object or person placed downstream of the device. This can be accomplished using a plasma device such as described by Ladwig et al (Surface & Coatings Technology 201 (2007) 6460-6464). Use of such a plasma device would allow the plasma to operate at frequencies below 100 kHz.

The plasma parameters (electrode design, frequency, voltage, gas composition, etc.) can be chosen to control the plasma process and ensure that the plasma operates in a non-thermal manner to produce a low-temperature plasma, which does not adversely affect temperature sensitive materials which are being deposited.

Furthermore, the precursor can be introduced downstream of the plasma chamber outlet to minimise damage to the coating forming materials. This allows coatings containing materials sensitive to temperature, ions, free radicals and other active species present in the plasma to be deposited where they would otherwise be damaged if introduced directly into the plasma chamber.

Various active compounds can be incorporated into the coating produced by this device. These can include anti-cancer drugs, anti-inflammatory drugs, immuno-suppressants, antibiotics, antimicrobials, heparin, a functional protein, a regulatory protein, structural proteins, oligo-peptides, antigenic peptides, nucleic acids, immunogens, glycosaminoglycans and combinations thereof.

Other active compounds include polypeptides, polyglycans, hormones, lipids, interferons, cartilage, therapeutic biologic agents both cellular and synthetically derived, autologous, homologous and allographic and zenographic biologic agents, autologous or homologous, recombinant and synthetic derived blood cells and products containing antimicrobiallantibiotic agents, bacteriostatic agents, stem cells, stromal cells; fibroblast derived Human Dermal Collagen, matrix proteins, growth factors and cytokines, fibronectin, cells found in loose connective tissue such as endothelial cells, cells found in adipose tissue, macrophages/monocytes, adipocytes, pericytes, reticular cells found in bone marrow stroma and cultured autologous keratinocytes.

In a preferred application, the wound is coated with a layer of either coagulated blood or blood extracts. The coating is produced by nebulising a supply of blood, or blood constituents, into the plasma chamber or into the species exiting from the plasma chamber. This offers a route to producing thin films, which are highly biocompatible and already contain the necessary factors (fibrin, cytokines, etc.) necessary to seal the wound and to induce wound healing.

Nonetheless, the nature of the deposited layer may be varied dependent on factors including: the underlying cause of the wound, the characteristics of the wound, the stage of wound healing, the particular patient needs and risk factors, availability of autologous materials.

Thus, different depositions can be used depending on whether wound healing is at the haemostasis, inflammation, proliferation/granulation or maturation/remodelling phase. Examples of materials for the various phases of wound healing include:

1. Fresh trauma/burns: Sealicontain wound with a temporary resorbable material containing appropriate active agents including, for example, antimicrobials, analgesics, vasoconstrictors in order to contain the wound while minimising dehydration/shock, pain, blood loss, risk of infection/contamination, further tissue loss, etc and initiating haemostasis.

2. Haemostasis stage: A resorbable material such as blood plasma or platelets including active agent(s) such as, vasoconstrictors, adenosine diphosphate (ADP), thrombin, fibrinogen/fibrin, cytokines (PDGF), chemotactic factors, chemocines or coagulation factors.

3. Inflammation stage: A resorbable material such as blood plasma including, for example, neutrophils, monocytes, phagocytes, mast cells, proteolytic enzymes, leukocytes.

4. Proliferation/granulation stage: A resorbable material including for:
   a. Granulation—macrophages. Fibroblastic Growth Factor (FGF), Epidermal Growth Factor (EGF), transforming growth factor beta (TGF-beta), Extra cellular matrix (ECM), fibroblasts, myofibroblasts
   b. Contracture—fibroblasts, collagen, endothelial cells, keratinocytes, angiocytes, neurocytes,
   c. Epithelisation—growth factors, fibrin, collagen, and fibronectin 5. Maturation/remodeling: Type I collagen.

6. Enhanced/accelerated wound healing or for large wound and burn injuries or chronic non-healing ulcers: Cytokines and growth factors Other applications including cornea regeneration using cytokines following abrasion or cataract treatment.

All variants may also provide the following:
A moisture retaining occlusive barrier and high humidity at the wound surface;
Gaseous exchange;
Thermal insulation; and
Protection against secondary infection Examples 1. Deposition of Blood Plasma Coating A biocompatible coating was deposited on to a glass slide using a non-thermal plasma discharge and blood plasma as the precursor. The plasma discharge was created by applying an alternating voltage to a corona needle electrode assembly within a dielectric housing. The voltage was applied at a frequency of 100 kHz from a Redline G2000 high voltage power supply. Helium was used as a ballast gas at a flow rate of 14 litres/minute. (It will be appreciated that other gases including argon or nitrogen or mixtures thereof could also be used.) The blood plasma extract was nebulised into the plasma using a Burgener pneumatic nebuliser (Burgener Research, Canada) at a flow rate of 51 microlitres/min. The input power was applied using a 45% duty cycle (ratio of time on to time off) and a selected input power on the power supply of 107 V. This corresponded to an actual applied voltage of 12.7 kV (pk-pk) applied to the electrodes. The substrate was a glass slide placed approximately 5 mm downstream of the plasma exit.

The blood plasma was sprayed through the plasma and landed upon the glass slide, where it coagulated instantly to form a coating. After deposition, the coating was inspected at a magnification of 40 times and the viable cell numbers were counted. Prior to being exposed to the electrical discharge, cell viability was estimated to be 90%. After undergoing nebulisation and plasma coagulation, over 70% of the cells were still deemed viable, indicating that biological materials have been successfully deposited intact and capable of participating in a biological healing process.

2. Deposition of a Biopolymer (Chitosan)

Chitson is known to have antimicrobial properties and is also a common scaffold material used in regenerative medicine. Water-soluble chitosan was dissolved in deionised water to give a concentration of 20 mg/ml. This liquid was introduced at 50 µL/min into the equipment described in Example 1 and coatings were deposited onto glass slides. Coatings were deposited at a power input setting of 170V and 150 kHz and for times of 45 seconds, 1 minute and 3 minutes. In each case, a clear coating was detected on the surface of the glass slide. This coating was not removed by wiping with a tissue, indicating that the coating was dry, cured and adherent.

3. Deposition of a Protein Solution (Collagen) at Low Frequency

Collagen is a known aid in wound healing process and is a key component of skin. A plasma device comprising a needle corona electrode powered by a 100 W Plasma Technics Inc power supply operating at c. 20 kHz was provided. Helium was introduced to the system at a rate of 8 litres/minute. An acidified solution of collagen (3.8 mgiml) was nebulised into the resultant discharge at a flow rate of 50 µL/min and coatings were deposited onto glass slides for 1-2 minutes. All deposits were found to be coherent, dry and adhered well to the substrate, indicating that a cured coating had been formed.

4. Deposition of a Protein Solution (Collagen) at High Frequency

A solution of collagen (1 mg/ml) was introduced into the equipment described in Example 1. The plasma was operated at 115V input power, 148 kHz and a duty cycle of 44%. Helium was introduced at a rate of 5 litres/min. The collagen solution was introduced at a rate of 50 pLimin and a coating was deposited onto polished Si wafers for either one minute or two minutes. Ellipsometry detected a coating with a thickness of 50 nm for the one minute sample and 140 nm for the two minute sample, confirming that a coating had been deposited.

What is claimed is:

1. A method for treating a patient, the method comprising:
   generating a non-thermal equilibrium plasma at a frequency between 100 kHz and 500 kHz via an electrode housed in a plasma chamber with a wall opposite an outlet exposed to ambient pressure, wherein the electrode extends through a first lumen parallel to a second lumen, wherein the wall defines an opening of the first lumen adjacent to an opening of the second lumen;
   introducing an aerosol comprising a bioresorbable material through the opening of the second lumen into the plasma chamber and the non-thermal equilibrium plasma through the distal opening of the second lumen; and contacting tissue of the patient with reactive species emanating from the plasma and with the aerosol downstream of the outlet to form a coating on the tissue, wherein the coating is bioresorbable.

2. The method of claim 1, wherein a distal tip of the electrode is proximate the wall of the plasma chamber opposite the outlet.

3. The method of claim 1, wherein the plasma is pulsed.

4. The method of claim 1, wherein the tissue is part of a wound, and contacting the tissue with the plasma sterilizes and coagulates the wound.

5. The method of claim 1, wherein the aerosol is generated from a liquid by a nebulizer, the bioresorbable material being dissolved or dispersed in the liquid.

6. The method of claim 1, wherein the bioresorbable material comprises a protein, a nucleic acid, a lipid, a drug, a polysaccharide, a biopolymer, a biodegradable polymer, a cell, or a combination thereof.

7. The method of claim 1, wherein the bioresorbable material comprises collagen, fibrin, fibronectin, chitin, hyaluronan, chitosan, alginate, cellulose, or a combination thereof.

8. The method of claim 1, wherein the bioresorbable material comprises blood plasma or a blood platelet.

9. The method of claim 1, wherein the bioresorbable material in the coating is biologically active.

10. The method of claim 1, wherein the bioresorbable material comprises:
 a. a biopolymer, a biodegradable polymer, a protein, or a combination thereof; and
 b. an antimicrobial, an analgesic, a vasoconstrictor, or a combination thereof.

11. A method for treating a patient, the method comprising:
 generating a non-thermal equilibrium plasma at a frequency between 100 kHz and 500 kHz via an electrode housed in a plasma chamber with a wall opposite an outlet exposed to ambient pressure, the wall defining a first opening containing a distal tip of the electrode and a second opening adjacent to the first opening, wherein the electrode extends through a first lumen parallel to a second lumen, the first lumen terminating at the first opening and the second lumen terminating at the second opening;
 introducing an aerosol comprising a bioresorbable material through the second opening into the plasma chamber and the non-thermal equilibrium plasma, such that the bioresorbable material contacts the non-thermal plasma within the plasma chamber and exits the plasma chamber with the non-thermal equilibrium plasma; and
 forming a coating comprising the bioresorbable material on tissue of the patient by directly contacting the tissue with the plasma and the aerosol downstream of the plasma chamber, wherein the tissue is part of a wound, wherein the coating is bioresorbable, and wherein the bioresorbable material in the coating is biologically-active.

12. The method of claim 11, wherein the coating seals the wound.

13. The method of claim 11, wherein the bioresorbable material in the coating is cross-linked.

14. The method of claim 11, wherein the plasma is pulsed.

* * * * *